United States Patent
Huang et al.

(10) Patent No.: US 6,972,416 B2
(45) Date of Patent: Dec. 6, 2005

(54) DISINFECTING AND DESICCATING CONTAINER FOR PERSONAL SANITARY ARTICLES

(76) Inventors: Ching-Chuan Huang, 11F-3, No. 73, Sec. 1, Wenshin Rd., Nam-Twen District, Taichuang (TW); Min-Tsung Huang, 11F-3, No. 73, Sec. 1, Wenshin Rd., Nam-Twen District, Taichuang (TW)

( * ) Notice: Subject to any disclaimer, the term of this patent is extended or adjusted under 35 U.S.C. 154(b) by 0 days.

(21) Appl. No.: 10/750,951

(22) Filed: Jan. 5, 2004

(65) Prior Publication Data

US 2005/0145801 A1    Jul. 7, 2005

(51) Int. Cl.[7] .............................. A61L 2/10; A61L 9/20
(52) U.S. Cl. .................................. 250/455.11; 422/24
(58) Field of Search ...................... 250/455.11; 422/24

(56) References Cited

U.S. PATENT DOCUMENTS

| | | | |
|---|---|---|---|
| 4,892,712 A | * | 1/1990 | Robertson et al. .......... 422/186 |
| 5,069,885 A | * | 12/1991 | Ritchie ...................... 422/186 |
| 5,487,877 A | * | 1/1996 | Choi .......................... 422/300 |
| 2004/0089815 A1 | * | 5/2004 | Woo ....................... 250/455.11 |
| 2004/0155201 A1 | * | 8/2004 | Russell et al. ......... 250/455.11 |

FOREIGN PATENT DOCUMENTS

WO    WO 9640430    *    6/1996

* cited by examiner

Primary Examiner—John R. Lee
Assistant Examiner—Jamesw J. Leybourne
(74) Attorney, Agent, or Firm—Rosenberg, Klein & Lee

(57) ABSTRACT

A disinfecting and desiccating container for personal sanitary articles includes a holding tray having an article receiving recess and a disinfecting energy irradiating area, an upper cover connected to a top of the holding tray, a disinfecting device provided at one side of the disinfecting energy irradiating area, and a power supply unit for supplying electric energy required by the disinfecting device to work. The disinfecting device includes a lighting tube coated with a layer of nanometer light-catalyzed material, so that the nanometer light-catalyzed material is catalyzed by light emitted from the lighting tube to generate disinfecting energy for disinfecting the personal sanitary articles held to the article receiving recess by a clamping member fitted in the holding tray.

6 Claims, 5 Drawing Sheets

DISINFECTING AND DESICCATING CONTAINER FOR PERSONAL SANITARY ARTICLES

BACKGROUND OF THE INVENTION

1. Field of the Invention

The present invention relates to a container for holding personal sanitary articles, and more particularly to an easily portable disinfecting and desiccating container adapted to effectively disinfect personal sanitary articles positioned therein.

2. Description of the Prior Art

There are a lot of articles, particularly those being frequently used in our daily life in wet conditions, that need disinfecting, desiccating, or heat drying from time to time, in order to prevent growth of bacteria on these articles to endanger the user's health. A toothbrush is one example of these articles and needs effective disinfection and desiccation. Ultraviolet sterilization, electric-heat drying, and fan drying are some common ways to disinfect and desiccate these articles. There are also various kinds of disinfecting or desiccating devices developed for this purpose. Taiwanese New Utility Model Patent published under No. 268239 discloses an ultraviolet sterilizing and drying box. A tubular ultraviolet lamp is mounted in the box below an upper cover thereof, and an electric-heater fan is mounted at a rectangular heat-dissipating window provided at a lower case of the box. When the ultraviolet lamp and the electric-heater fan are turned on, a toothbrush positioned in the disinfecting box can be disinfected and heat dried.

Taiwanese New Utility Model Patent published under No. 180870 also discloses a microphone-disinfecting box. The box is provided at a front end with a tubular ultraviolet lamp. A light-transmissible plate is located behind the ultraviolet lamp and enclosed by reflective metal plates, so that an area evenly reflecting ultraviolet is formed. Aromatic compound is positioned in the box. When a fan in the box operates, sweet air from the aromatic compound is sucked into the box via a vent to achieve the freshening and deodorizing effect.

Most products in the prior art related to heat drying and disinfection use the ultraviolet lamp to achieve the function of disinfection. However, only very limited disinfecting effect may be achieved with these conventional products.

Moreover, most of the conventional heat drying and disinfecting boxes are not conveniently portable and can therefore be used indoor typically at a certain fixed position. There is not any disinfecting and desiccating device suitable for disinfecting and desiccating personal sanitary articles, such as a toothbrush, frequently carried for use by students, office workers, and travelers when they are not at home. People would simply position these personal sanitary articles in a box to carry along with them. The personal sanitary articles positioned in a normal closed box tend to be contaminated by bacteria.

It is therefore desirable to develop a disinfecting and desiccating container for personal sanitary articles, so that people may conveniently carry their personal sanitary articles with them without the problem in disinfecting and desiccating these articles from time to time.

SUMMARY OF THE INVENTION

A primary object of the present invention is to provide a disinfecting and desiccating container for personal sanitary articles capable of disinfecting personal sanitary articles positioned therein.

Another object of the present invention is to provide a disinfecting and desiccating container for personal sanitary articles that can be conveniently carried along with a user to disinfect and desiccate personal sanitary articles positioned therein at any time and at any place.

A further object of the present invention is to provide a disinfecting and desiccating container for personal sanitary articles that uses disinfecting energy generated by a nanometer light-catalyzed material to provide good disinfecting effect on personal sanitary articles carried with the container.

To achieve the objects, the present invention includes a holding tray having an article receiving recess and a disinfecting energy irradiating area, an upper cover connected to a top of the holding tray, a disinfecting device provided at one side of the disinfecting energy irradiating area, and a power supply unit for supplying electric energy required by the disinfecting device to work. The disinfecting device includes a lighting tube coated with a layer of nanometer light-catalyzed material, so that the nanometer light-catalyzed material is catalyzed by light emitted from the lighting tube to generate disinfecting energy for disinfecting the personal sanitary articles held to the article receiving recess by a clamping member fitted in the holding tray.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
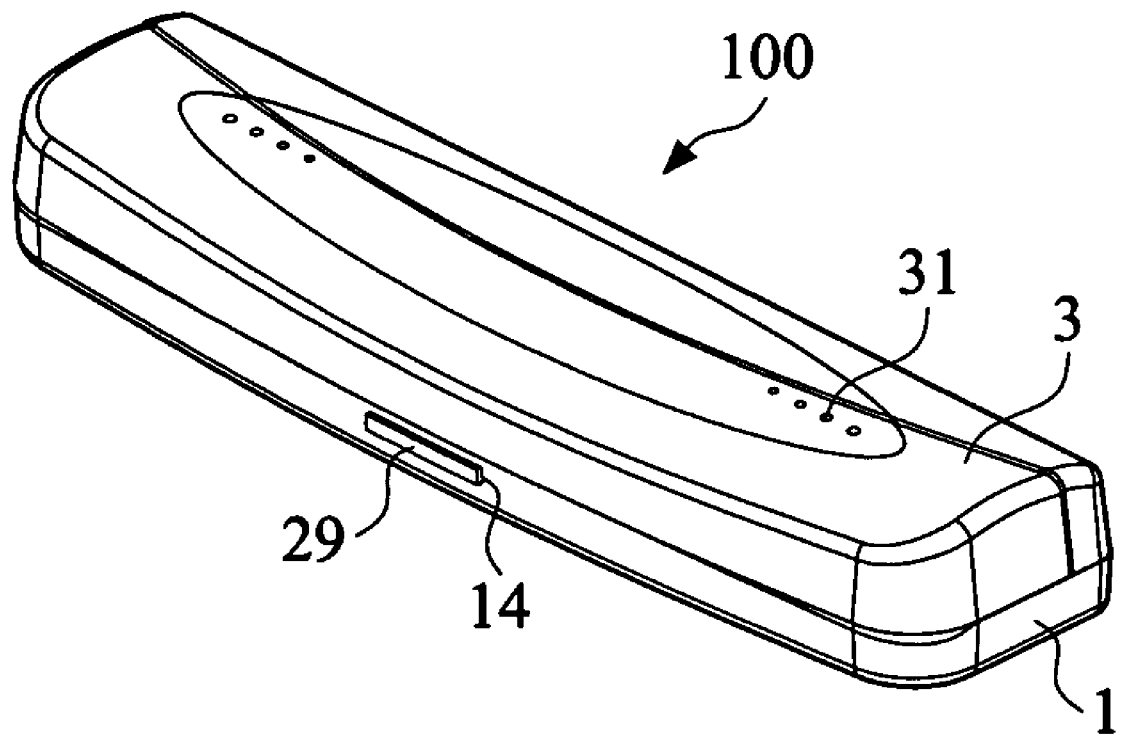
FIG. 1 is an assembled perspective view of a disinfecting and desiccating container for personal sanitary articles according to the present invention.
Figure 2:
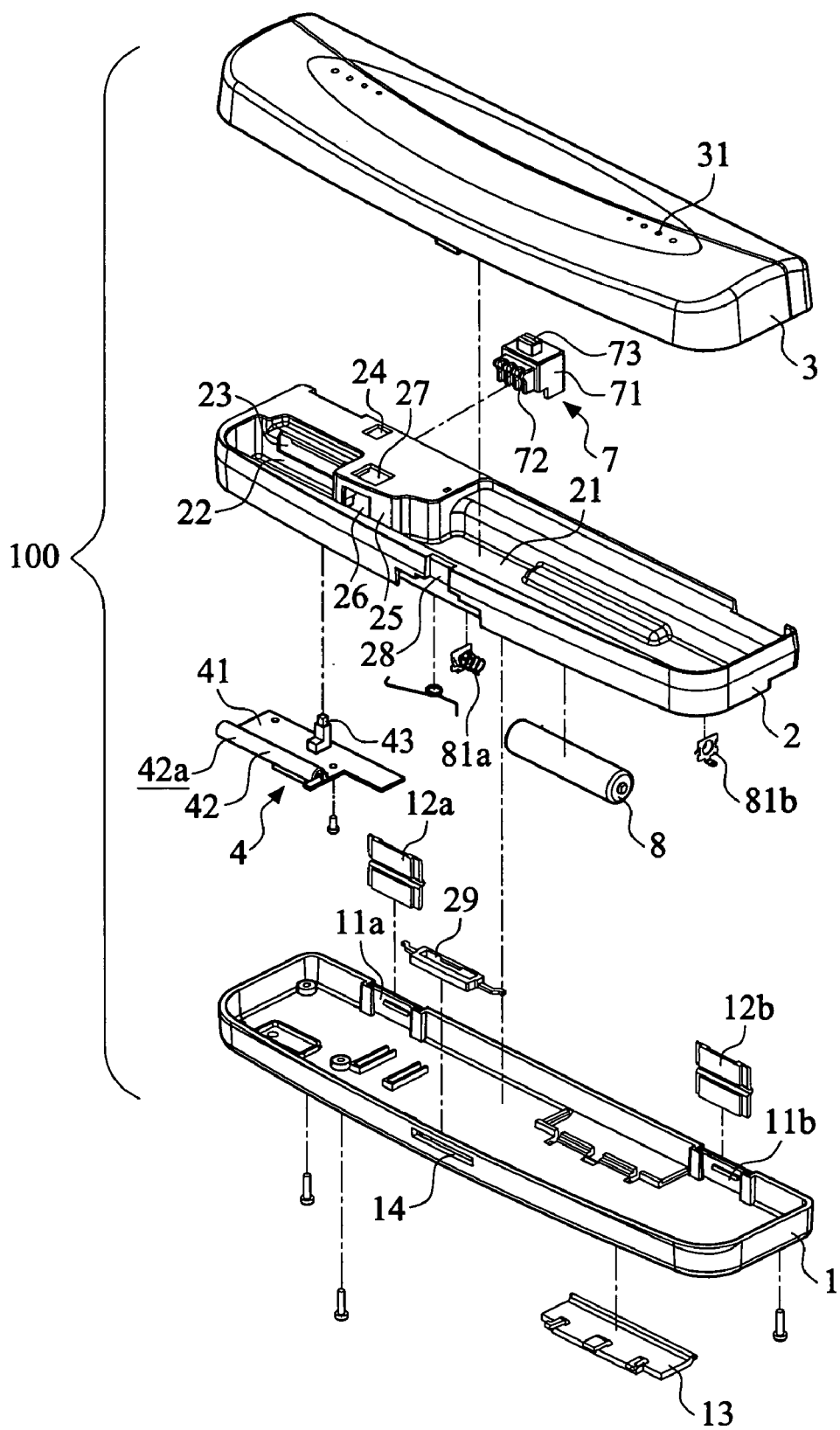
FIG. 2 is an exploded perspective view of FIG. 1 showing different components of the present invention.

Please refer to FIGS. 1 and 2 that are assembled and exploded perspective views, respectively, of a disinfecting and desiccating container for personal sanitary articles according to the present invention. For simplicity, the present invention will be briefly referred to as the container 100 hereinafter. As shown, the container 100 mainly includes a lower cover 1, a holding tray 2 located in the lower cover 1, and an upper cover 3.

The lower cover 1 is provided at a rear edge with a pair of locating recesses 11a, 11b for two connecting members 12a, 12b to set therein, so that the upper cover 3 is pivotally connected at a rear edge to the lower cover 1 via the connecting members 12a; 12b to be lifted from or closed to the lower cover 1. When the upper cover 3 is closed to the lower cover 1, a closed receiving space is defined between the lower and the upper cover 1, 3.

Figure 3:
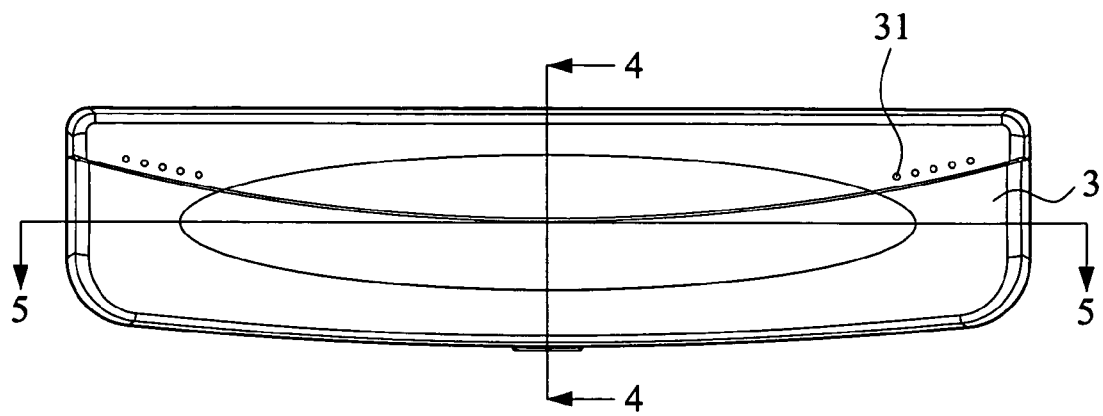
FIG. 3 is a top view of the present invention.
Figure 4:
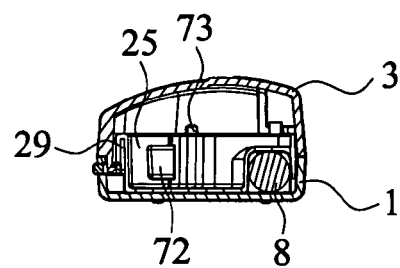
FIG. 4 is a sectional view taken along line 4—4 of FIG. 3.
Figure 5:
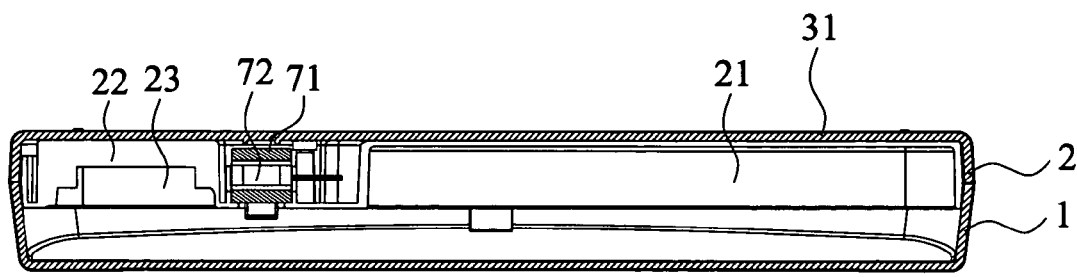
FIG. 5 is a sectional view taken along line 5—5 of FIG. 3.

Please also refer to FIGS. 3, 4, and 5 that are sequentially a top view of the container 100, a cross sectional view taken along line 4—4 of FIG. 3, and a cross sectional view taken along line 5-5 of FIG. 3.

The holding tray 2 is provided at one end with an article-receiving recess 21, and at the other end with a disinfecting energy irradiating area 22. At a predetermined position of the disinfecting energy irradiating area 22, there is provided with an opening for a light-transmissible board 23 to associate therewith.

A disinfecting means 4 is provided to one side of the disinfecting energy irradiating area 22 of the holding tray 2, so that disinfecting energy generated by the disinfecting means 4 passes through the light-transmissible board 23 into the disinfecting energy irradiating area 22.

Figure 6:
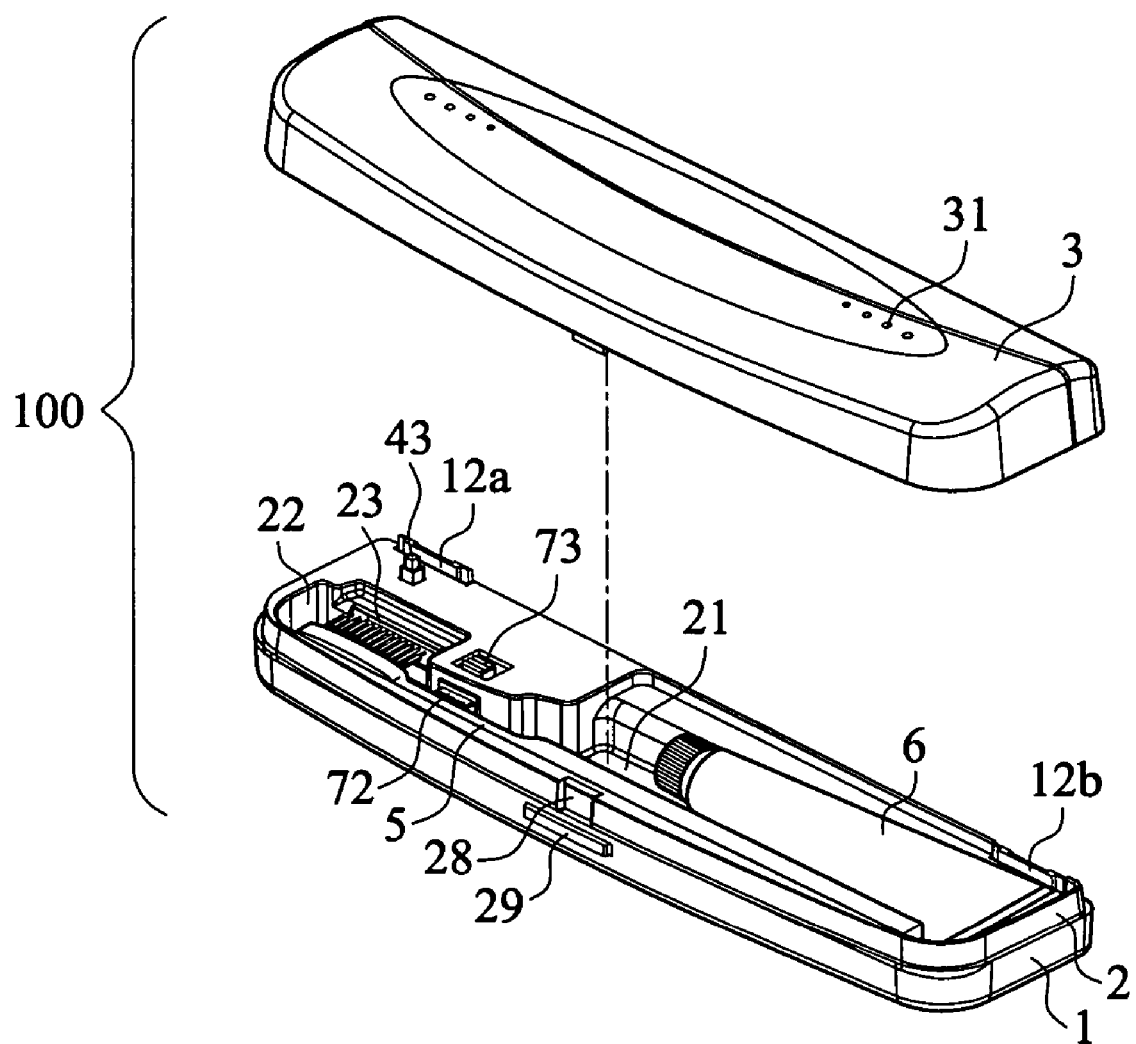
FIG. 6 is a perspective view showing a toothbrush is positioned in an article-receiving recess on a holding tray of the present invention.

Please refer to FIG. 6. A personal sanitary article, such as a toothbrush 5, may be positioned in the article receiving recess 21 of the holding tray 2 with a handle of the toothbrush 5 received in the article receiving recess 21 and a brush block of the toothbrush 5 located in the disinfecting energy irradiating area 22 to face toward the light-transmissible board 23. In addition to the toothbrush 5, there is still enough space in the article receiving recess 21 for receiving other articles, such as a tube of toothpaste 6.

In a preferred embodiment of the present invention, the disinfecting means 4 includes a circuit board 41, a lighting tube as light source 42 coated with a layer of nanometer (nm) light-catalyzed material 42a, and a contact on/off switch 43. The disinfecting means 4 is mounted at a predetermined position in the holding tray 2, so that the contact on/off switch 43 projects from an opening 24 formed on the holding tray 2 by a predetermined height. When the upper cover 3 is closed to locate above the holding tray 2, the contact on/off switch 43 is contact with and depressed by the closed upper cover 3 to actuate the disinfecting means 4 for the same to start a disinfecting function. When the disinfecting means 4 is actuated, it generates an amount of disinfecting energy that passes through the light-transmissible board 23 into the disinfecting energy irradiating area 22 to disinfect the brush block of the toothbrush 5.

Figure 7:
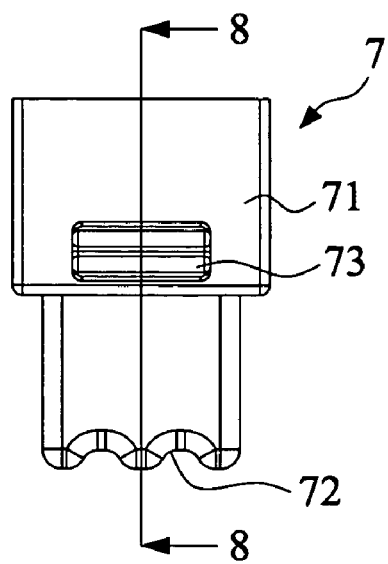
FIG. 7 is a top view of a clamping member of the present invention.
Figure 8:
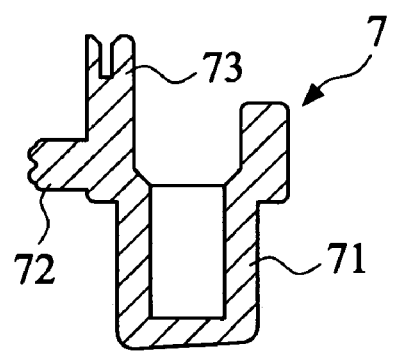
FIG. 8 is a sectional view taken along line 8—8 of FIG. 7.

The holding tray 2 is provided near a middle section with a narrowed area 25 substantially corresponding to a neck portion of the toothbrush 5. A clamping member 7 is mounted adjacent to one side of the narrowed area 25. Please refer to FIGS. 7 and 8 at the same time. The clamping member 7 includes a main body 71, an article-contacting clamp head 72 provided at a front end of the main body 71, and a locating protrusion 73 formed at a top of the main body 71. The clamping member 7 is so positioned that the main body 71 is located below the holding tray 2 with the clamp head 72 sideward projected through an opening 26 into the narrowed area 25 by a predetermined length, and the locating protrusion 73 upward projected through another opening 27 provided on a top of the holding tray and firmly held thereto. The clamp head 72 sideward projected from the opening 26 into the narrowed area 25 is adapted to stably hold the toothbrush 5 in place in the holding tray 2.

A power supply unit, such as a battery 8, is mounted in a battery compartment provided between the holding tray 2 and the lower cover 1. The battery 8 is electrically connected at two ends to two metal contacts 81a, 81b provided below the holding tray 2, so that power is supplied from the battery 8 to the container 100 for the same to work. A battery compartment door 13 is detachably connected to the lower cover 1 to enclose the battery 8 in the battery compartment.

The holding tray 2 is provided at a front edge with a fastening recess 28. An elastic member 29 is provided between the holding tray 2 and the lower cover 1 to slightly project from a slot 14 provided on a front edge of the lower cover 1. The upper cover 3 may be closed onto the lower cover 1 and firmly held thereto via the elastic member 29. When the elastic member 29 is depressed from outside of the container 100, the upper cover 3 is automatically released from the lower cover 1 and could be lifted.

The upper cover 3 is provided with at least one vent 31 to enable proper venting of the container 100.

In addition to the disinfecting function provided by the nanometer light-catalyzed layer 42a on the lighting tube 42, the container 100 also provides other functions. For example, a proper heating element may be provided in the disinfecting means 4 or other suitable position in the container 100 to produce heat energy for desiccating or heat drying the personal sanitary article positioned in the container 100.

The present invention has been described with a preferred embodiment thereof and it is understood that many changes and modifications in the described embodiment can be carried out without departing from the scope and the spirit of the invention that is to be limited only by the appended claims.

What is claimed is:

1. A disinfecting and desiccating container, comprising:
a holding tray having an article receiving recess and a disinfecting energy irradiating area formed thereon, the article receiving recess being provided with a clamping member for holding a personal sanitary article in place in the article receiving recess;
an upper cover associated with and located above the holding tray, so that a closed receiving space is defined between the upper cover and the holding tray;
a disinfecting means for supplying a disinfecting energy, provided in the holding tray adjacent to the disinfecting energy irradiating area; and
a power supply unit for supplying electric energy to the disinfecting means; whereby when the personal sanitary article is positioned in the article receiving recess of the holding tray, the disinfecting means generates the disinfecting energy through the disinfecting energy irradiating area to the personal sanitary article.

2. The disinfecting and desiccating container as claimed in claim 1, wherein the disinfecting energy irradiating area is adjacent to a light-transmissable board located in an opening formed on the holding tray.

3. The disinfecting and desiccating container as claimed in claim 1, wherein upper cover is provided with at least one vent.

4. The disinfecting and desiccating container as claimed in claim 1, wherein the disinfecting means comprises a contact on/off switch that is located between the holding tray and the upper cover and adapted to actuate the power supply unit to automatically supply power to the disinfecting means for generating the disinfecting energy when the upper cover is closed onto the holding tray to contact with the on/off switch.

5. The disinfecting and desiccating container as claimed in claim 1, wherein the clamping member comprises a main body, an article-contacting clamp head provided at a front end of the main body, and a locating protrusion formed at a top of the main body; and the main body being firmly set in the holding tray with the clamp head sideward projected into the article receiving recess by a predetermined length to hold the personal sanitary article in place in the holding tray, and the locating protrusion upward projected through a top of the holding tray to be firmly held thereto.

6. The disinfecting and desiccating container as claimed in claim 1, further comprising a lower cover mounted to the holding tray, so that the holding tray is stably supported on the lower cover.

* * * * *